(12) United States Patent
Gibson

(10) Patent No.: US 9,565,828 B2
(45) Date of Patent: Feb. 14, 2017

(54) REPUBLIC LETTUCE VARIETY

(71) Applicant: PROGENY ADVANCED GENETICS, Salinas, CA (US)

(72) Inventor: George Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 14/710,461

(22) Filed: May 12, 2015

(65) Prior Publication Data

US 2015/0327506 A1    Nov. 19, 2015

Related U.S. Application Data

(60) Provisional application No. 61/993,872, filed on May 15, 2014.

(51) Int. Cl.
*A01H 5/12* (2006.01)

(52) U.S. Cl.
CPC ........................................ *A01H 5/12* (2013.01)

(58) Field of Classification Search
None
See application file for complete search history.

(56) References Cited

U.S. PATENT DOCUMENTS 8,835,719 B2 * 9/2014 Gibson ................... A01H 5/12
435/410

* cited by examiner

*Primary Examiner* — Eileen B O Hara
(74) *Attorney, Agent, or Firm* — Morrison & Foerster LLP

(57) ABSTRACT

A new lettuce variety designated 'Republic' is described. 'Republic' is an iceberg lettuce variety exhibiting stability and uniformity.

11 Claims, No Drawings

REPUBLIC LETTUCE VARIETY

CROSS REFERENCE TO RELATED APPLICATION

This application claims the benefit under 35 §USC 119(e) of U.S. Provisional Patent Application No. 61/993,872, filed May 15, 2014, the disclosure of which is hereby incorporated by reference in its entirety.

FIELD

This invention relates to the field of plant breeding. In particular, this invention relates to new lettuce, *Lactuca sativa*, variety, 'Republic'.

BACKGROUND

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

SUMMARY

In order to meet these needs, the present invention is directed to an improved iceberg lettuce variety that exhibits vigorous growth, increased weight, and increased yield. In particular, the present invention is directed to lettuce, *Lactuca sativa*, seed designated as 'Republic' having ATCC Accession Number PTA-122194. The present invention is further directed to a *Lactuca sativa* plant produced by growing 'Republic' lettuce seed having ATCC Accession Number PTA-122194. The present invention is further directed to a lettuce head isolated from a *Lactuca sativa* plant produced by growing 'Republic' lettuce seed having ATCC Accession Number PTA-122194. The present invention is further directed to a *Lactuca sativa* plant having all the physiological and morphological characteristics of a *Lactuca sativa* plant produced by growing 'Republic' lettuce seed having ATCC Accession Number PTA-122194. The present invention is further directed to an $F_1$ hybrid *Lactuca sativa* plant having 'Republic' as a parent, where 'Republic' lettuce seed is grown from 'Republic' seed having ATCC Accession Number PTA-122194.

The present invention is further directed to lettuce, *Lactuca sativa* plants and lettuce heads isolated therefrom produced by growing 'Republic' lettuce seed. The present invention is further directed to a *Lactuca sativa* plant and the lettuce head isolated therefrom having all the physiological and morphological characteristics of a *Lactuca sativa* plant produced by growing 'Republic' lettuce seed having ATCC Accession Number PTA-122194. The present invention is further directed to an $F_1$ hybrid lettuce, *Lactuca sativa* plant and a head isolated therefrom grown from the seed having 'Republic' as a parent wherein 'Republic' is grown from 'Republic' lettuce seed having ATCC Accession Number PTA-122194.

The present invention is further directed to pollen isolated from 'Republic' lettuce plants. The present invention is further directed to ovules isolated from 'Republic' lettuce plants. The present invention is further directed to tissue culture of 'Republic' lettuce plants.

The present invention is further directed to a method of selecting lettuce comprising a) growing Republic lettuce plants wherein the plants are grown from lettuce seed having ATCC Accession Number PTA-122194 and b) selecting a plant from step a). The present invention is further directed to lettuce plants and seeds produced there from wherein the lettuce plant is isolated by the selection method of the invention. The present invention is further directed to a method of selecting lettuce plants by: a) growing more than one 'Republic' lettuce plant, where the plants are grown from lettuce seed having ATCC Accession Number PTA-122194; and b) selecting a plant from step a). The present invention is further directed to lettuce plants and seeds produced therefrom, where the lettuce plants and seeds are isolated by the selection method of the invention.

The present invention is further directed to a method of breeding lettuce by crossing a lettuce plant with a plant grown from 'Republic' lettuce seed having ATCC Accession Number PTA-122194. The present invention is further directed to lettuce plants, heads isolated therefrom, and seeds produced therefrom, where the lettuce plant is isolated by the breeding method of the invention.

DETAILED DESCRIPTION

Definitions

In order to more clearly understand the invention, the following definitions are provided:

Iceberg Lettuce: Iceberg lettuce, *Lactuca sativa* L. var. *capitala* L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Average Head Diameter: Average head diameter is an average of the measured head diameter and head length of the lettuce head.

Average Head Diameter: Core Length Ratio: The ratio of the average head diameter to core length is indicative of the percentage of usable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

Taking into account these definitions, the present invention is directed to seeds of the lettuce variety 'Republic', plants produced by growing 'Republic' lettuce seeds, head isolated or harvested from the plants, one or more plants selected from a collection of 'Republic' plants and seeds derived or produced therefrom; plants produced by crossing a lettuce plant with a 'Republic' lettuce plant and seeds derived or produced therefrom.

Origin and Breeding History of the Variety 'Republic'

'Republic' is an iceberg lettuce variety that is distinct to all known iceberg lettuce varieties due to its large heading, and improved tip burn and bolting resistance for plantings in regions such as California's southern Salinas valley and Yuma, Ariz.

'Republic', is an iceberg lettuce variety developed from a hand pollinated cross of two iceberg lettuce varieties adapted to warm production regions. The female parent PSJV032083, is a proprietary breeding line adapted to the early September plantings in the desert south west, and the male parent PSJV032084, is an iceberg lettuce breeding line adapted to summer harvest in south Monterey county, California. The two parental varieties were selected for their specific adaptability and physiological resistances, and their respective yield potential. Through the single seed descent and pedigree selection breeding methods, 'Republic' was developed as a larger heading, tip burn and bolting resistant lettuce variety for the summer production regions of California's southern Salinas valley, and the spring harvest period of Yuma, Ariz.'s production region.

In Year 1, in a summer research seed production field in California's San Joaquin valley a cross was made of the proprietary breeding lines PSJV032083 and PSJV032084. The F1 seed was harvested in August of year one, and designated as PSJV032083XPSJV032084.

In October of Year 1, forty F1 seeds of PSJV032083XPSJV032084 were planted in a green house facility in San Juan Bautista, Calif., indicated by the research line number PSJB032319. At market maturity all apparent self-pollinated plants were removed and the remaining F1 plants were allowed to self-pollinate. The F2 seed was harvested in bulk in late April of Year 2. The seed was immediately cleaned, processed, blended, and prepared for planting.

Two hundred random F2 seeds of line number PSJB032319 were planted in a summer research seed production field and re-designated as PSJV042985 in the spring of Year 2. Segregation amongst the F2 population was noted and all plants were allowed to self-pollinate and produce seed. The F3 seed from each plant was harvested and packaged individually in the fall of Year 2. One seed from each package (plant) was removed and placed in one envelope, designated as PAUS043608, and planted again in a research production field in Australia in October of Year 3. Observations were performed at the research production field in Australia, where segregation for phenotype and maturity was again evident and noted, and all plants were allowed to self-pollinate and produce seed. F4 seed from 100 individual plants was harvested, cleaned, and packaged individually. The packets were shipped from Australia to Salinas, Calif. for processing.

The 100 F4 lines, all from non-selected single F3 plants of the pedigree PSJV032083XPSJV032084, were processed in California in the summer of Year 4. A trial was prepared containing each of the 100 F4 individual lines of the designated pedigree, using the parent varieties and industry standard varieties as checks for the desired attributes. A research trial was planted in King City, Calif. in July of Year 4 where the lines could be evaluated for the desired heat resistant traits. The trial was evaluated in September of Year 4. All F4 lines were evaluated based on phenotypic uniformity, improved size, improved weight, improved frame size, and resistance to tip burn and core length, when compared to the parent and check varieties. Twelve F4 lines of this pedigree were selected as they outperformed the parent varieties, their sibs, and the majority of other lines in the trial for the designated traits. The line PAUS 043608-57 was among the 12 F4 lines advanced.

Seed from these 12 F4 lines were then increased in a Year 4 research and development seed production field in Australia. A sample of the remnant F4 seed from PAUS 043608-57, designated as PAUS054577 was planted in a research seed production field in October of Year 4. The block contained roughly 200 plants, which were rogued for phenotype and maturity at various stages of growth, all offtypes and variants were removed. The remaining plants in the block were allowed to self-pollinate, and the F5 seed from the block was harvested in mass in spring of Year 5.

Three trials of the 12 advanced breeding lines, parent lines, and commercial standard varieties, containing roughly 300 plants each were planted in the summer of Year 5 in the southern region of the Salinas valley, California for further evaluation for the desired traits. Evaluations of the trials were conducted in September and October of Year 5. All 12 F5 advanced breeding lines were evaluated based on phenotypic uniformity, improved weight, improved frame size, improved leaf texture and resistance to tip burn and bolting, when compared to the parent and check varieties. Four of the twelve F5 advanced breeding lines continually outperformed the parent lines and the check varieties for the desired traits and were advanced. Among the four lines advanced was line number PAUS054577.

A portion of the remnant F5 seed from the four advanced lines was again increased in a Year 6 San Joaquin valley, California research and development seed production field. Roughly 200 plants of each line were grown. Line PAUS054577, was redesignated as PSJV075480, and all lines were rogued at multiple stages of development for phenotypic uniformity, head size, frame size, and timing of bolting and flowering. The PSJV075480 line was noted to be uniform, stable, and free of variants during the production cycle. The F6 seed of the four lines was harvested as a priority in August Year 6, and was cleaned and processed. Multiple trials of the four F6 lines, including PSJV075480, were conducted in the warmer regions of the Salinas valley, California, again side by side with the parent varieties and commercial standard varieties for comparison purposes. Line PSJV075480 continually outperformed its siblings, its parents, and the standard check varieties for overall appearance, leaf texture, frame size, and resistance to tip burn and bolting. Based on the trial results, line PSJV075480 was advanced through the research process and designated as PX 1565.

Large trials of PX 1565 were then conducted in multiple lettuce production regions, including the southern region or the Salinas valley, California, and for the spring harvest slot in the Yuma production regions of Arizona. The variety continued to perform and the F6 generation of the variety was evaluated to be uniform, stable, and free of variants. An additional small increase of seed was made in a summer research and development seed production field in the San Joaquin valley, California, F7 seed was harvested in the fall of Year 6. Based on the continued performance of the variety PX 1583, seed was then commercially increased in year 7.

Multiple individual plant selections were made during the commercial increase of the variety, selections were made based on slower maturity, slower bolting, and larger head size. Among the selections, a plant labeled SJV10126-5 was selected and the seed was harvested individually. This F8 individual plant selection was trialed in the summer in the southern Salinas valley, California, and in the spring in Yuma, Ariz., where it demonstrated excellent uniformity, and was larger heading, slower maturing, had a lower core, and no tip burn when compared to PX 1565. The F8 seed was increased in Year 8, and the F9 bulk seed harvested was designated PSJV118570.

Following numerous trials in Year 9 in the King City area of the Salinas valley, California, and in the spring harvest slot in Yuma, Ariz., PSJV118570 was designated PX 1620. F10 seed of PX 1620 was increased in Year 9 and trialed in Year 10, again demonstrating a larger head size than PX 1565, as well as being slower maturing, having a lower core, and free of tip burn. The F11 seed was increased in preparation to launch the variety in Year 10, and in trials, continues to demonstrate the improved selected traits. The variety PX 1620 was named 'Republic' in September of Year 10.

As evaluated in large trials and in seed production fields, 'Republic' has been observed for two generations to be uniform and stable without variants.

As described herein, lettuce variety 'Republic' has numerous distinguishing characteristics.

A. Variety Description Information

| Plant Type: | Iceberg |
|---|---|
| Seed: | |
| Seed Color: | White |
| Light Dormancy: | No |
| Heat Dormancy: | Yes |
| Cotyledons: | |
| Shape of Cotyledons: | Intermediate |
| Shape of Fourth Leaf: | Spatulate |
| Length/Width Index of Fourth Leaf: | 22 |
| Apical Margin: | Moderately Dentate |
| Basal Margin: | Finley Dentate |
| Undulation: | Medium |
| Green Color: | Medium |
| Anthocyanin: | Absent |
| Distribution: | None |
| Rolling: | Absent |
| Cupping: | Uncupped |
| Reflexing: | Slight |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Dark |
| Anthocyanin: | |
| Distribution: | None |
| Size: | Large |
| Glossiness: | Moderate |
| Blistering: | Moderate |
| Leaf Thickness: | Thick |
| Trichomes: | Absent |

B. Comparison to Most Similar Variety

| Characteristic | 'Republic' | 'Salute' |
|---|---|---|
| Spread of Frame Leaves | 39 cm | 35 cm |
| Head Diameter (market trimmed with single cup leaf) | 15 cm | 13 cm |
| Head Shape | Spherical | Spherical |
| Head Size Class | Large | Medium |
| Head Count per Carton | 24 | 24 |
| Head Weight | 975 | 840 |
| Head Firmness | Firm | Firm |
| Butt | | |
| Shape | Rounded | Rounded |
| Midrib | Flat | Flat |
| Core (Stem of Market-trimmed Head) | | |
| Diameter at the base of the Head | 4.0 cm | 4.0 cm |
| Ratio of Head Diameter/Core Diameter | 3.75 | 3.25 |
| Core Height from base of Head to Apex | 3.0 cm | 4.0 cm |
| Number of Days from First Water Date to Seed Stalk Emergence (Summer condition) | 75 | 71 |
| Bolting Class | Very Slow | Slow |
| Height of Mature Seed Stalk | 126 cm | 131 cm |
| Spread of Bolter Plant | 36 cm | 38 cm |
| Bolter Leaves | Curved | Curved |
| Margin | Dentate | Dentate |
| Color | Dark Green | Dark Green |
| Bolter Habit | | |
| Terminal Inflorescence | Present | Present |
| Lateral Shoots (above head) | Absent | Absent |
| Basal Side Shoots | Absent | Absent |
| Adaptation Regions | Salinas Valley, CA and Yuma, AZ | Salinas Valley, CA and Yuma, AZ |

C. Growing Season

| Season | 'Republic' | 'Salute' |
|---|---|---|
| Spring area | Desert South West | Desert South West |
| Summer area | Salinas Valley | Salinas Valley |
| Fall area | Not Adapted | Not Adapted |
| Winter area: | Not Adapted | Not Adapted |

D. Diseases and Stress Reactions

| Disease or Stress | 'Republic' | 'Salute' |
|---|---|---|
| Virus | N/A | N/A |
| Big Vein: | Susceptible | Susceptible |
| Lettuce Mosaic: | Susceptible | Susceptible |

E. Fungi/Bacteria

| Fungal/Bacterial | 'Republic' | 'Salute' |
|---|---|---|
| Corky Root Rot (*Pythium* Root Rot): | Susceptible | Susceptible |
| Downy Mildew (Races I, IIA, III): | Susceptible | Susceptible |
| Powdery Mildew: | Susceptible | Susceptible |
| *Sclerotinia* Rot: | Intermediate | Intermediate |
| Bacterial Soft Rot (*Pseudomonas* spp. & others): Not tested | Susceptible | Susceptible |
| *Botrytis* (Gray Mold): | Susceptible | Susceptible |
| Other: Corky Root Rot (*Rhizomonas suberifaciens*): | Susceptible | Susceptible |

F. Insects

| Insects | 'Republic' | 'Salute' |
| --- | --- | --- |
| Cabbage Loopers: | Susceptible | Susceptible |
| Root Aphids: | Susceptible | Susceptible |
| Green Peach Aphid: | Susceptible | Susceptible |

G. Physiological/Stress

| Stress | 'Republic' | 'Salute' |
| --- | --- | --- |
| Tipburn | Resistant | Resistant |
| Heat | Resistant | Resistant |
| Drought | Susceptible | Susceptible |
| Cold | Susceptible | Susceptible |
| Salt | Susceptible | Susceptible |

H. Post Harvest

| Characteristic | 'Republic' | 'Salute' |
| --- | --- | --- |
| Pink Rib | Moderately Susceptible | Moderately Susceptible |
| Russet Spotting | Moderately Susceptible | Moderately Susceptible |
| Rusty Brown Discoloration | Moderately Susceptible | Moderately Susceptible |
| Internal Rib Necrosis (Blackheart, Gray Rib, Gray Streak) | Moderately Susceptible | Moderately Susceptible |

Breeding and Selection

The present invention is further directed to the use of 'Republic' lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Ariz. and Huron, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

In addition to manual removal of anther tubes, a modified method of misting to wash the pollen off prior to fertilization may be used to assure crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

A deposit of the lettuce variety 'Republic' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

At least 2500 seeds of lettuce variety 'Republic' were deposited on Jun. 1, 2015 according to the Budapest Treaty in the American Type Culture Collection (ATCC), ATCC Patent Depository, 10801 University Boulevard, Manassas, Va., 20110, USA. The deposit has been assigned ATCC number PTA-122194. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed for the enforceable life of the patent.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

This invention will be better understood by reference to the following non-limiting Examples.

EXAMPLES

Example 1

General Trialing Method

The following steps illustrate the general trialing method of the invention:

I. Set Up

1. A trial is set up to compare one or more lines. Parental lines and related varieties are identified.
2. Primary slots are identified.

3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as other lettuce plants in the commercial field.
2. The trial is thinned to separate the plants for optimum growth.

Example 2

Comparative Analysis

'Republic' is a new and distinct variety of iceberg lettuce that most closely resembles the variety 'PX 1565'. 'Republic' is a Salinas type iceberg lettuce variety adapted to warmer lettuce production regions of the Salinas valley, California, and the spring harvest period of the Yuma, Ariz. production region. 'Republic' is a larger heading and large framed variety, with excellent heading characteristics, head shape, leaf texture and significantly improved resistance to tip burn and bolting.

'Republic' is slower maturing, larger heading, slower bolting and has better tip burn resistance than PX 1565.
Evaluation of Head Size Diameter Measured to the Nearest 1 mm

TABLE 1A

| Trial | 1 | | 2 | | 3 | |
|---|---|---|---|---|---|---|
| Wet/Eval Date | Aril 18 | June 23 | April 23 | June 30 | May 10 | July 14 |
| Location | Salinas Valley | | Salinas Valley | | Salinas Valley | |
| Plant | Head Diam. (mm) | | Head Diam. (mm) | | Head Diam. (mm) | |
|  | 'Republic' | 'Salute' | 'Republic' | 'Salute' | 'Republic' | 'Salute' |
| 1 | 148.0 | 136.0 | 142.0 | 135.0 | 147.0 | 132.0 |
| 2 | 147.0 | 142.0 | 142.0 | 130.0 | 147.0 | 135.0 |
| 3 | 146.0 | 136.0 | 145.0 | 135.0 | 145.0 | 135.0 |
| 4 | 148.0 | 145.0 | 145.0 | 135.0 | 145.0 | 134.0 |
| 5 | 148.0 | 142.0 | 148.0 | 134.0 | 147.0 | 134.0 |
| 6 | 145.0 | 142.0 | 145.0 | 133.0 | 142.0 | 136.0 |
| 7 | 147.0 | 138.0 | 147.0 | 135.0 | 147.0 | 133.0 |
| 8 | 147.0 | 136.0 | 142.0 | 136.0 | 148.0 | 133.0 |
| 9 | 148.0 | 137.0 | 145.0 | 136.0 | 145.0 | 135.0 |
| 10 | 145.0 | 140.0 | 148.0 | 140.0 | 146.0 | 132.0 |
| 11 | 146.0 | 140.0 | 148.0 | 132.0 | 149.0 | 132.0 |
| 12 | 151.0 | 142.0 | 145.0 | 135.0 | 149.0 | 134.0 |
| 13 | 143.0 | 141.0 | 145.0 | 134.0 | 148.0 | 134.0 |
| 14 | 146.0 | 142.0 | 148.0 | 136.0 | 146.0 | 133.0 |
| 15 | 148.0 | 145.0 | 148.0 | 134.0 | 143.0 | 133.0 |
| 16 | 148.0 | 136.0 | 149.0 | 137.0 | 144.0 | 133.0 |
| 17 | 149.0 | 132.0 | 150.0 | 137.0 | 148.0 | 135.0 |
| 18 | 149.0 | 135.0 | 150.0 | 135.0 | 144.0 | 138.0 |
| 19 | 150.0 | 138.0 | 148.0 | 135.0 | 146.0 | 133.0 |
| 20 | 145.0 | 136.0 | 147.0 | 132.0 | 145.0 | 132.0 |
| 21 | 144.0 | 138.0 | 145.0 | 132.0 | 148.0 | 134.0 |
| 22 | 147.0 | 141.0 | 148.0 | 135.0 | 149.0 | 133.0 |
| 23 | 146.0 | 140.0 | 149.0 | 134.0 | 150.0 | 133.0 |
| 24 | 145.0 | 138.0 | 149.0 | 133.0 | 150.0 | 132.0 |
| 25 | 145.0 | 138.0 | 146.0 | 138.0 | 148.0 | 130.0 |
| 26 | 149.0 | 132.0 | 142.0 | 132.0 | 149.0 | 133.0 |
| 27 | 148.0 | 136.0 | 147.0 | 132.0 | 154.0 | 134.0 |
| 28 | 151.0 | 135.0 | 142.0 | 134.0 | 148.0 | 137.0 |
| 29 | 145.0 | 140.0 | 142.0 | 135.0 | 149.0 | 132.0 |
| 30 | 147.0 | 138.0 | 148.0 | 132.0 | 148.0 | 130.0 |
| Average | 147.0 | 138.6 | 146.2 | 134.4 | 147.1 | 133.5 |
| Stan dev | 1.97E+00 | 3.31E+00 | 2.60E+00 | 2.10E+00 | 2.43E+00 | 1.76E+00 |
| T test | 2.00E−06 | | 7.42E−27 | | 1.05E−32 | |
| Probability % | 100.0 | | 100.0000 | | 100.0000 | |
| % Difference | 6.1 | | 8.7 | | 10.2 | |
| Confidence Int | 0.0226 | 0.0379 | 0.0298 | 0.0240 | 0.0278 | 0.0201 |
| Range of Var min* | 147.01 | 138.53 | 146.14 | 134.41 | 147.11 | 133.45 |
| Range of Var max* | 147.06 | 138.60 | 146.20 | 134.46 | 147.16 | 133.49 |

*Range of variation among means of statistically significant differences at the 95% level using the confidence interval [C] = mean +/− {SDXSE}.

TABLE 1B

| Trial | 4 | | 5 | | 6 | |
|---|---|---|---|---|---|---|
| Wet/Eval Date | Dec. 18 | April 2 | Dec. 263 | April 3 | Jan. 9 | April 10 |
| Location | Yuma | | Yuma | | Yuma | |
| Plant | Head Diam. (mm) | | Head Diam. (mm) | | Head Diam. (mm) | |
| | 'Republic' | 'Salute' | 'Republic' | 'Salute' | 'Republic' | 'Salute' |
| 1 | 150.0 | 141.0 | 148.0 | 130.0 | 145.0 | 132.0 |
| 2 | 150.0 | 142.0 | 148.0 | 130.0 | 145.0 | 131.0 |
| 3 | 150.0 | 140.0 | 147.0 | 130.0 | 147.0 | 135.0 |
| 4 | 152.0 | 140.0 | 149.0 | 130.0 | 148.0 | 134.0 |
| 5 | 152.0 | 142.0 | 145.0 | 132.0 | 148.0 | 133.0 |
| 6 | 154.0 | 142.0 | 145.0 | 132.0 | 145.0 | 134.0 |
| 7 | 153.0 | 142.0 | 146.0 | 135.0 | 145.0 | 135.0 |
| 8 | 152.0 | 145.0 | 146.0 | 134.0 | 147.0 | 140.0 |
| 9 | 156.0 | 140.0 | 149.0 | 136.0 | 145.0 | 141.0 |
| 10 | 154.0 | 142.0 | 148.0 | 133.0 | 145.0 | 135.0 |
| 11 | 152.0 | 132.0 | 148.0 | 136.0 | 148.0 | 138.0 |
| 12 | 150.0 | 136.0 | 146.0 | 133.0 | 149.0 | 136.0 |
| 13 | 150.0 | 138.0 | 145.0 | 135.0 | 145.0 | 132.0 |
| 14 | 154.0 | 140.0 | 147.0 | 132.0 | 150.0 | 132.0 |
| 15 | 152.0 | 140.0 | 148.0 | 132.0 | 152.0 | 130.0 |
| 16 | 154.0 | 138.0 | 146.0 | 130.0 | 151.0 | 132.0 |
| 17 | 152.0 | 138.0 | 148.0 | 130.0 | 154.0 | 130.0 |
| 18 | 151.0 | 136.0 | 148.0 | 135.0 | 149.0 | 134.0 |
| 19 | 151.0 | 140.0 | 148.0 | 130.0 | 148.0 | 133.0 |
| 20 | 152.0 | 142.0 | 148.0 | 130.0 | 150.0 | 135.0 |
| 21 | 151.0 | 136.0 | 147.0 | 135.0 | 151.0 | 136.0 |
| 22 | 154.0 | 138.0 | 146.0 | 135.0 | 152.0 | 133.0 |
| 23 | 158.0 | 138.0 | 145.0 | 130.0 | 145.0 | 133.0 |
| 24 | 156.0 | 136.0 | 145.0 | 130.0 | 148.0 | 132.0 |
| 25 | 152.0 | 132.0 | 142.0 | 135.0 | 148.0 | 133.0 |
| 26 | 152.0 | 134.0 | 147.0 | 134.0 | 149.0 | 135.0 |
| 27 | 151.0 | 140.0 | 144.0 | 132.0 | 145.0 | 134.0 |
| 28 | 153.0 | 132.0 | 142.0 | 134.0 | 150.0 | 133.0 |
| 29 | 153.0 | 132.0 | 146.0 | 133.0 | 151.0 | 132.0 |
| 30 | 152.0 | 130.0 | 144.0 | 133.0 | 153.0 | 130.0 |
| Average | 152.4 | 138.1 | 146.4 | 132.5 | 148.3 | 133.8 |
| Stan dev | 1.94E+00 | 3.81E+00 | 1.85E+00 | 2.15E+00 | 2.73E+00 | 2.62E+00 |
| T test | 8.89E−26 | | 2.49E−34 | | 8.93E−29 | |
| Probability % | 100.0000 | | 100.0000 | | 100.0000 | |
| % Difference | 10.4 | | 10.4 | | 10.8 | |
| Confidence Int | 0.0222 | 0.0436 | 0.0211 | 0.0246 | 0.0312 | 0.0300 |
| Range of Var min* | 152.41 | 138.09 | 146.35 | 132.51 | 148.24 | 133.74 |
| Range of Var max* | 152.46 | 138.18 | 146.39 | 132.56 | 148.30 | 133.80 |

*Range of variation among means of statistically significant differences at the 95% level using the confidence interval [C] = mean +/− {SDXSE}.

As shown in the results listed in Tables 1A and 1B, the average head size of 'Republic' is significantly larger than that of 'Salute'.

Evaluation of Presence of Tip Burn

TABLE 2A

| Trial No. | 1 | | 2 | | 3 | |
|---|---|---|---|---|---|---|
| Wet/Eval Date | April 18 | June 23 | April 23 | June 30 | May 10 | July 14 |
| Location | Salinas Valley | | Salinas Valley | | Salinas Valley | |
| Plant | Tip Burn Incidence | | Tip Burn Incidence | | Tip Burn Incidence | |
| | 'Republic' | 'Salute' | 'Republic' | 'Salute' | 'Republic' | 'Salute' |
| 1 | 0.0 | 0.0 | 0.0 | 1.0 | 0.0 | 0.0 |
| 2 | 0.0 | 0.0 | 0.0 | 0.0 | 0.0 | 0.0 |
| 3 | 0.0 | 0.0 | 0.0 | 0.0 | 0.0 | 0.0 |
| 4 | 0.0 | 0.0 | 0.0 | 0.0 | 0.0 | 0.0 |
| 5 | 0.0 | 0.0 | 0.0 | 0.0 | 0.0 | 0.0 |
| 6 | 0.0 | 1.0 | 0.0 | 0.0 | 0.0 | 0.0 |
| 7 | 0.0 | 0.0 | 0.0 | 0.0 | 0.0 | 0.0 |
| 8 | 0.0 | 0.0 | 0.0 | 0.0 | 0.0 | 0.0 |
| 9 | 0.0 | 0.0 | 0.0 | 0.0 | 0.0 | 1.0 |
| 10 | 0.0 | 0.0 | 0.0 | 0.0 | 0.0 | 0.0 |
| 11 | 0.0 | 0.0 | 0.0 | 1.0 | 0.0 | 0.0 |
| 12 | 0.0 | 0.0 | 0.0 | 0.0 | 0.0 | 0.0 |
| 13 | 0.0 | 0.0 | 0.0 | 0.0 | 0.0 | 0.0 |

TABLE 2A-continued

| Trial No. | 1 | | 2 | | 3 | |
|---|---|---|---|---|---|---|
| Wet/Eval Date | April 18 | June 23 | April 23 | June 30 | May 10 | July 14 |
| Location | Salinas Valley | | Salinas Valley | | Salinas Valley | |
| Plant | Tip Burn Incidence | | Tip Burn Incidence | | Tip Burn Incidence | |
| | 'Republic' | 'Salute' | 'Republic' | 'Salute' | 'Republic' | 'Salute' |
| 14 | 0.0 | 1.0 | 0.0 | 0.0 | 0.0 | 0.0 |
| 15 | 0.0 | 0.0 | 0.0 | 0.0 | 0.0 | 0.0 |
| 16 | 0.0 | 0.0 | 0.0 | 0.0 | 0.0 | 0.0 |
| 17 | 0.0 | 0.0 | 0.0 | 0.0 | 0.0 | 0.0 |
| 18 | 0.0 | 0.0 | 0.0 | 0.0 | 0.0 | 0.0 |
| 19 | 0.0 | 1.0 | 0.0 | 0.0 | 0.0 | 0.0 |
| 20 | 0.0 | 0.0 | 0.0 | 0.0 | 0.0 | 0.0 |
| 21 | 0.0 | 0.0 | 0.0 | 0.0 | 0.0 | 0.0 |
| 22 | 0.0 | 0.0 | 0.0 | 0.0 | 0.0 | 1.0 |
| 23 | 0.0 | 0.0 | 0.0 | 1.0 | 0.0 | 0.0 |
| 24 | 0.0 | 0.0 | 0.0 | 0.0 | 0.0 | 0.0 |
| 25 | 0.0 | 1.0 | 0.0 | 0.0 | 0.0 | 0.0 |
| 26 | 0.0 | 0.0 | 0.0 | 0.0 | 0.0 | 0.0 |
| 27 | 0.0 | 0.0 | 0.0 | 0.0 | 0.0 | 0.0 |
| 28 | 0.0 | 0.0 | 0.0 | 0.0 | 0.0 | 0.0 |
| 29 | 0.0 | 0.0 | 0.0 | 0.0 | 0.0 | 1.0 |
| 30 | 0.0 | 0.0 | 0.0 | 0.0 | 0.0 | 0.0 |
| Total infected | 0.0 | 4.0 | 0.0 | 3.0 | 0.0 | 3.0 |
| Stan dev | 0.00E+00 | 3.46E−01 | 0.00E+00 | 3.05E−01 | 0.00E+00 | 3.05E−01 |
| T test | 3.90E−02 | | 7.79E−02 | | 7.79E−02 | |
| Probability % | 96.10 | | 92.21 | | 92.21 | |
| Difference | 100.0 | | 100.0 | | 100.0 | |
| Confidence Int | 0.0000 | 0.0040 | 0.0000 | 0.0035 | 0.0000 | 0.0035 |
| Range of Var min* | 0.00 | 4.00 | 0.00 | 3.00 | 0.00 | 3.00 |
| Range of Var max* | 0.00 | 4.00 | 0.00 | 3.00 | 0.00 | 3.00 |

*Range of variation among means of statistically significant differences at the 95% level using the confidence interval [C] = mean +/− {SDXSE}.

TABLE 2B

| Trial No. | 4 | | 5 | | 6 | |
|---|---|---|---|---|---|---|
| Wet/Eval Date | Dec. 18 | April 2 | Dec. 26 | April 3 | Jan. 9 | April 10 |
| Location | Yuma | | Yuma | | Yuma | |
| Plant | Tip Burn Incidence | | Tip Burn Incidence | | Tip Burn Incidence | |
| | 'Republic' | 'Salute' | 'Republic' | 'Salute' | 'Republic' | 'Salute' |
| 1 | 0.0 | 0.0 | 0.0 | 0.0 | 0.0 | 0.0 |
| 2 | 0.0 | 0.0 | 0.0 | 0.0 | 0.0 | 0.0 |
| 3 | 0.0 | 0.0 | 0.0 | 0.0 | 0.0 | 0.0 |
| 4 | 0.0 | 0.0 | 0.0 | 0.0 | 0.0 | 0.0 |
| 5 | 0.0 | 0.0 | 0.0 | 0.0 | 0.0 | 0.0 |
| 6 | 0.0 | 1.0 | 0.0 | 0.0 | 0.0 | 0.0 |
| 7 | 0.0 | 1.0 | 0.0 | 0.0 | 0.0 | 1.0 |
| 8 | 0.0 | 1.0 | 0.0 | 1.0 | 0.0 | 0.0 |
| 9 | 0.0 | 0.0 | 0.0 | 0.0 | 0.0 | 0.0 |
| 10 | 0.0 | 0.0 | 0.0 | 0.0 | 0.0 | 0.0 |
| 11 | 0.0 | 0.0 | 0.0 | 0.0 | 0.0 | 0.0 |
| 12 | 0.0 | 0.0 | 0.0 | 0.0 | 0.0 | 0.0 |
| 13 | 0.0 | 0.0 | 0.0 | 0.0 | 0.0 | 0.0 |
| 14 | 0.0 | 0.0 | 0.0 | 1.0 | 0.0 | 0.0 |
| 15 | 0.0 | 0.0 | 0.0 | 0.0 | 0.0 | 0.0 |
| 16 | 0.0 | 0.0 | 0.0 | 0.0 | 0.0 | 0.0 |
| 17 | 0.0 | 0.0 | 0.0 | 0.0 | 0.0 | 0.0 |
| 18 | 0.0 | 1.0 | 0.0 | 0.0 | 0.0 | 0.0 |
| 19 | 0.0 | 0.0 | 0.0 | 0.0 | 0.0 | 0.0 |
| 20 | 0.0 | 0.0 | 0.0 | 0.0 | 0.0 | 0.0 |
| 21 | 0.0 | 0.0 | 0.0 | 0.0 | 0.0 | 0.0 |
| 22 | 0.0 | 0.0 | 0.0 | 0.0 | 0.0 | 1.0 |
| 23 | 0.0 | 0.0 | 0.0 | 0.0 | 0.0 | 0.0 |
| 24 | 0.0 | 0.0 | 0.0 | 1.0 | 0.0 | 0.0 |
| 25 | 0.0 | 0.0 | 0.0 | 0.0 | 0.0 | 0.0 |
| 26 | 0.0 | 0.0 | 0.0 | 0.0 | 0.0 | 0.0 |
| 27 | 0.0 | 0.0 | 0.0 | 0.0 | 0.0 | 0.0 |
| 28 | 0.0 | 0.0 | 0.0 | 0.0 | 0.0 | 0.0 |

TABLE 2B-continued

| Trial No. | 4 | | 5 | | 6 | |
|---|---|---|---|---|---|---|
| Wet/Eval Date | Dec. 18 | April 2 | Dec. 26 | April 3 | Jan. 9 | April 10 |
| Location | Yuma | | Yuma | | Yuma | |
| Plant | Tip Burn Incidence | | Tip Burn Incidence | | Tip Burn Incidence | |
| | 'Republic' | 'Salute' | 'Republic' | 'Salute' | 'Republic' | 'Salute' |
| 29 | 0.0 | 0.0 | 0.0 | 0.0 | 0.0 | 0.0 |
| 30 | 0.0 | 0.0 | 0.0 | 0.0 | 0.0 | 0.0 |
| Total infected | 0.0 | 4.0 | 0.0 | 3.0 | 0.0 | 2.0 |
| Stan dev | 0.00E+00 | 3.46E−01 | 0.00E+00 | 3.05E−01 | 0.00E+00 | 2.54E−01 |
| T test | 3.90E−02 | | 7.79E−02 | | 1.55E−01 | |
| Probability % | 96.10 | | 92.21 | | 84.45 | |
| Difference | 100.0 | | 100.0 | | 100.0 | |
| Confidence Int | 0.0000 | 0.0040 | 0.0000 | 0.0035 | 0.0000 | 0.0029 |
| Range of Var min* | 0.00 | 4.00 | 0.00 | 3.00 | 0.00 | 2.00 |
| Range of Var max* | 0.00 | 4.00 | 0.00 | 3.00 | 0.00 | 2.00 |

*Range of variation among means of statistically significant differences at the 95% level using the confidence interval [C] = mean +/− {SDXSE}.

In Tables 2A and 2B, tip burn incidence is rated as absent or present. If tip burn is absent in a head, a 0 is recorded. If tip burn is present in a head then a 1 is recorded.

As shown in the results listed in Tables 2A and 2B, none of the 'Republic' plants in any of the 6 trials has tip burn, as compared to 'Salute', which had an average of 3 plants per trial with tip burn.

Evaluation of Tip Burn Severity

TABLE 3A

| Trial No. | 1 | | 2 | | 3 | |
|---|---|---|---|---|---|---|
| Wet/Eval Date | April 18 | June 23 | April 23 | June 30 | May 10 | July 14 |
| Location | Salinas Valley | | Salinas Valley | | Salinas Valley | |
| Plant | Tip Burn Severity | | Tip Burn Severity | | Tip Burn Severity | |
| | 'Republic' | 'Salute' | 'Republic' | 'Salute' | 'Republic' | 'Salute' |
| 1 | 0.0 | 0.0 | 0.0 | 1.0 | 0.0 | 0.0 |
| 2 | 0.0 | 0.0 | 0.0 | 0.0 | 0.0 | 0.0 |
| 3 | 0.0 | 0.0 | 0.0 | 0.0 | 0.0 | 0.0 |
| 4 | 0.0 | 0.0 | 0.0 | 0.0 | 0.0 | 0.0 |
| 5 | 0.0 | 0.0 | 0.0 | 0.0 | 0.0 | 0.0 |
| 6 | 0.0 | 2.0 | 0.0 | 0.0 | 0.0 | 0.0 |
| 7 | 0.0 | 0.0 | 0.0 | 0.0 | 0.0 | 0.0 |
| 8 | 0.0 | 0.0 | 0.0 | 0.0 | 0.0 | 0.0 |
| 9 | 0.0 | 0.0 | 0.0 | 0.0 | 0.0 | 2.0 |
| 10 | 0.0 | 0.0 | 0.0 | 0.0 | 0.0 | 0.0 |
| 11 | 0.0 | 0.0 | 0.0 | 2.0 | 0.0 | 0.0 |
| 12 | 0.0 | 0.0 | 0.0 | 0.0 | 0.0 | 0.0 |
| 13 | 0.0 | 0.0 | 0.0 | 0.0 | 0.0 | 0.0 |
| 14 | 0.0 | 2.0 | 0.0 | 0.0 | 0.0 | 0.0 |
| 15 | 0.0 | 0.0 | 0.0 | 0.0 | 0.0 | 0.0 |
| 16 | 0.0 | 0.0 | 0.0 | 0.0 | 0.0 | 0.0 |
| 17 | 0.0 | 0.0 | 0.0 | 0.0 | 0.0 | 0.0 |
| 18 | 0.0 | 0.0 | 0.0 | 0.0 | 0.0 | 0.0 |
| 19 | 0.0 | 2.0 | 0.0 | 0.0 | 0.0 | 0.0 |
| 20 | 0.0 | 0.0 | 0.0 | 0.0 | 0.0 | 0.0 |
| 21 | 0.0 | 0.0 | 0.0 | 0.0 | 0.0 | 0.0 |
| 22 | 0.0 | 0.0 | 0.0 | 0.0 | 0.0 | 2.0 |
| 23 | 0.0 | 0.0 | 0.0 | 1.0 | 0.0 | 0.0 |
| 24 | 0.0 | 2.0 | 0.0 | 0.0 | 0.0 | 0.0 |
| 25 | 0.0 | 0.0 | 0.0 | 0.0 | 0.0 | 0.0 |
| 26 | 0.0 | 0.0 | 0.0 | 0.0 | 0.0 | 0.0 |
| 27 | 0.0 | 0.0 | 0.0 | 0.0 | 0.0 | 0.0 |
| 28 | 0.0 | 0.0 | 0.0 | 0.0 | 0.0 | 0.0 |
| 29 | 0.0 | 0.0 | 0.0 | 0.0 | 0.0 | 1.0 |
| 30 | 0.0 | 0.0 | 0.0 | 0.0 | 0.0 | 0.0 |
| Average | 0.0 | 0.3 | 0.0 | 0.1 | 0.0 | 0.2 |
| Stan dev | 0.00E+00 | 6.91E−01 | 0.00E+00 | 4.34E−01 | 0.00E+00 | 5.31E−01 |
| T test | 3.90E−02 | | 9.79E−02 | | 9.07E−02 | |
| Probability % | 96.10 | | 90.21 | | 90.93 | |
| Difference | 100.0 | | 100.0 | | 100.0 | |
| Confidence Int | 0.0000 | 0.0079 | 0.0000 | 0.0050 | 0.0000 | 0.0061 |

TABLE 3A-continued

| Trial No. | 1 | | 2 | | 3 | |
|---|---|---|---|---|---|---|
| Wet/Eval Date | April 18 | June 23 | April 23 | June 30 | May 10 | July 14 |
| Location | Salinas Valley | | Salinas Valley | | Salinas Valley | |
| Plant | Tip Burn Severity | | Tip Burn Severity | | Tip Burn Severity | |
| | 'Republic' | 'Salute' | 'Republic' | 'Salute' | 'Republic' | 'Salute' |
| Range of Var min* | 0.00 | 0.26 | 0.00 | 0.13 | 0.00 | 0.16 |
| Range of Var max* | 0.00 | 0.27 | 0.00 | 0.14 | 0.00 | 0.17 |

*Range of variation among means of statistically significant differences at the 95% level using the confidence interval [C] = mean +/− {SDXSE}.

TABLE 3B

| Trial No. | 4 | | 5 | | 6 | |
|---|---|---|---|---|---|---|
| Wet/Eval Date | Dec. 18 | April 2 | Dec. 26 | April 3 | Jan. 9 | April 10 |
| Location | Yuma | | Yuma | | Yuma | |
| Plant | Tip Burn Severity | | Tip Burn Severity | | Tip Burn Severity | |
| | 'Republic' | 'Salute' | 'Republic' | 'Salute' | 'Republic' | 'Salute' |
| 1 | 0.0 | 0.0 | 0.0 | 0.0 | 0.0 | 0.0 |
| 2 | 0.0 | 0.0 | 0.0 | 0.0 | 0.0 | 0.0 |
| 3 | 0.0 | 0.0 | 0.0 | 0.0 | 0.0 | 0.0 |
| 4 | 0.0 | 0.0 | 0.0 | 0.0 | 0.0 | 0.0 |
| 5 | 0.0 | 0.0 | 0.0 | 0.0 | 0.0 | 0.0 |
| 6 | 0.0 | 2.0 | 0.0 | 0.0 | 0.0 | 0.0 |
| 7 | 0.0 | 1.0 | 0.0 | 0.0 | 0.0 | 1.0 |
| 8 | 0.0 | 2.0 | 0.0 | 2.0 | 0.0 | 0.0 |
| 9 | 0.0 | 0.0 | 0.0 | 0.0 | 0.0 | 0.0 |
| 10 | 0.0 | 0.0 | 0.0 | 0.0 | 0.0 | 0.0 |
| 11 | 0.0 | 0.0 | 0.0 | 0.0 | 0.0 | 0.0 |
| 12 | 0.0 | 0.0 | 0.0 | 0.0 | 0.0 | 0.0 |
| 13 | 0.0 | 0.0 | 0.0 | 0.0 | 0.0 | 0.0 |
| 14 | 0.0 | 0.0 | 0.0 | 1.0 | 0.0 | 0.0 |
| 15 | 0.0 | 0.0 | 0.0 | 0.0 | 0.0 | 0.0 |
| 16 | 0.0 | 0.0 | 0.0 | 0.0 | 0.0 | 0.0 |
| 17 | 0.0 | 0.0 | 0.0 | 0.0 | 0.0 | 0.0 |
| 18 | 0.0 | 1.0 | 0.0 | 0.0 | 0.0 | 0.0 |
| 19 | 0.0 | 0.0 | 0.0 | 0.0 | 0.0 | 0.0 |
| 20 | 0.0 | 0.0 | 0.0 | 0.0 | 0.0 | 0.0 |
| 21 | 0.0 | 0.0 | 0.0 | 0.0 | 0.0 | 0.0 |
| 22 | 0.0 | 0.0 | 0.0 | 0.0 | 0.0 | 2.0 |
| 23 | 0.0 | 0.0 | 0.0 | 0.0 | 0.0 | 0.0 |
| 24 | 0.0 | 0.0 | 0.0 | 2.0 | 0.0 | 0.0 |
| 25 | 0.0 | 0.0 | 0.0 | 0.0 | 0.0 | 0.0 |
| 26 | 0.0 | 0.0 | 0.0 | 0.0 | 0.0 | 0.0 |
| 27 | 0.0 | 0.0 | 0.0 | 0.0 | 0.0 | 0.0 |
| 28 | 0.0 | 0.0 | 0.0 | 0.0 | 0.0 | 0.0 |
| 29 | 0.0 | 0.0 | 0.0 | 0.0 | 0.0 | 0.0 |
| 30 | 0.0 | 0.0 | 0.0 | 0.0 | 0.0 | 0.0 |
| Average | 0.0 | 0.2 | 0.0 | 0.2 | 0.0 | 0.1 |
| Stan dev | 0.00E+00 | 5.51E−01 | 0.00E+00 | 5.31E−01 | 0.00E+00 | 4.03E−01 |
| T test | 5.15E−02 | | 9.07E−02 | | 1.79E−01 | |
| Probability % | 94.85 | | 90.93 | | 82.11 | |
| Difference | 100.0 | | 100.0 | | 100.0 | |
| Confidence Int | 0.0000 | 0.0063 | 0.0000 | 0.0061 | 0.0000 | 0.0046 |
| Range of Var min* | 0.00 | 0.19 | 0.00 | 0.16 | 0.00 | 0.10 |
| Range of Var max* | 0.00 | 0.21 | 0.00 | 0.17 | 0.00 | 0.10 |

*Range of variation among means of statistically significant differences at the 95% level using the confidence interval [C] = mean +/− {SDXSE}.

In Tables 3A and 3B, tip burn severity is rated on a scale of 1-5, with "0" indicating no tip burn, "1" indicating slight decay, and "5" indicating most severe decay.

As shown in the results listed in Tables 3A and 3B, none of the 'Republic' plants in any of the trials showed tip burn (i.e., severity score of 0), while certain plants of 'Salute' in each of the trials displayed tip burn with a severity ranging from 1 to 2.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. *Lactuca sativa* seed designated as 'Republic', representative sample of seed having been deposited under ATCC Accession Number PTA-122194.

2. A *Lactuca sativa* plant produced by growing the seed of claim 1.

3. A lettuce head isolated from the plant of claim 2.

4. A *Lactuca sativa* plant having all the physiological and morphological characteristics of the *Lactuca sativa* plant of claim 2.

5. Pollen of the plant of claim 2.

6. An ovule of the plant of claim 2.

7. Tissue culture of the plant of claim 2.

8. An $F_1$ hybrid *Lactuca sativa* plant having 'Republic' as a parent where 'Republic' is grown from the seed of claim 1.

9. A method of selecting lettuce, comprising:
   a) growing more than one plant from the seed of claim 1; and
   b) selecting a plant from step a).

10. A *Lactuca sativa* plant selected by the method of claim 9.

11. *Lactuca sativa* seed produced from the *Lactuca sativa* plant of claim 10.

\* \* \* \* \*